United States Patent [19]

Musser

[11] 4,158,014
[45] Jun. 12, 1979

[54] 4-(HYDRAZONOMETHYL)BENZOIC ACID HYDRAZIDE

[75] Inventor: Harry R. Musser, Kingsport, Tenn.

[73] Assignee: Eastman Kodak Company, Rochester, N.Y.

[21] Appl. No.: 931,226

[22] Filed: Aug. 7, 1978

[51] Int. Cl.² ............................................. C07C 109/10
[52] U.S. Cl. ............................. 260/558 H; 528/367
[58] Field of Search .................................... 260/558 H

[56] References Cited

U.S. PATENT DOCUMENTS

| | | | |
|---|---|---|---|
| 3,459,799 | 8/1969 | Gutmann et al. | 260/558 H |
| 3,795,678 | 3/1974 | Bollag et al. | 260/558 H X |
| 3,931,268 | 1/1976 | Bollag et al. | 260/558 H X |

FOREIGN PATENT DOCUMENTS

| | | | |
|---|---|---|---|
| 1470154 | 2/1967 | France | 260/558 H |

*Primary Examiner*—Thomas Waltz
*Attorney, Agent, or Firm*—Daniel B. Reece, III; Charles R. Martin

[57] ABSTRACT

Disclosed is 4-(hydrazonomethyl)benzoic acid hydrazide having the structure

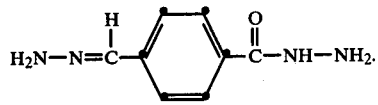

This compound can be prepared from methyl formyl benzoate and hydrazine. This compound can be prepared into a polymer by condensation with difunctional acid chlorides. Films of the polymer have unobviously high tensile and tear strengths without the necessity of biaxially orienting the film.

1 Claim, No Drawings

4-(HYDRAZONOMETHYL)BENZOIC ACID HYDRAZIDE

This invention is a compound which can be called 4-(hydrazonomethyl)benzoic acid hydrazide. Films prepared from a polymer of this compound exhibit commercially acceptable tensile and tear properties without biaxially orienting the film.

Films of synthetic polymers have been known and used commercially for decades. Originally films were used primarily for photographic films, pressure sensitive tape and other specialized applications. Subsequently the use of films expanded, particularly in packaging applications. Today, the use of films for photographic films, tapes, packaging and the like is enormous.

Although the physical properties required in a film vary somewhat depending on its application, almost all films are required to have high tensile strength and high tear strength so as to have good resistance to pulling and tearing loads.

Although synthetic polymers typically have fairly high values of tensile strength and tear strength, there is so little polymer in a film that the total tensile or tear load the film will support is fairly low. One solution to this problem is to stretch the polymer in both directions so as to orient the molecular chains and increase the tensile and tear strengths. This process is well known in the art and is often called biaxial orientation.

Applicant has now invented a compound which can be polymerized with difunctional acid chlorides. Films of the polymer have very high tensile and tear strength without the necessity of biaxial orienting. In addition, the films have an overall balance of properties which are desirable for typical film applications.

The 4-(hydrazonomethyl)benzoic acid hydrazide having the structure

can be prepared by contacting hydrazine and methyl formyl benzoate in an inert reaction solvent at suitable thermodynamic conditions for a suitable time in accordance with the following reaction:

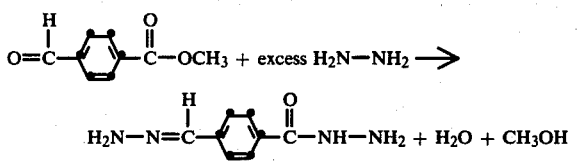

The hydrazine and methyl formyl benzoate can be contacted in a wide variety of well-known inert reaction solvents, such as alcohols and chlorinated aromatic compounds. The contact between hydrazine and methyl formyl benzoate can be accomplished by known methods, such as the dropwise addition of methyl formyl benzoate, dissolved in a suitable solvent, into stirred, refluxing hydrazine. The temperature used for contact can vary widely and should be hot enough for the reaction to procede within a reasonable time. The time required will, of course, depend on the temperature and other factors.

A specific example of the preparation of 4-(hydrazonomethyl)benzoic acid hydrazide is given below.

To a 2-liter flask fitted with stirrer, dropping funnel, and Soxhlett extractor containing 3 Å molecular sieves is charged 1000 ml. of absolute ethanol and 128 grams (4 moles) of 95 percent by weight hydrazine. With stirring the solution is taken to reflux and, over a period of 2 hours, 82 grams (0.5 mole) of methyl formyl benzoate dissolved in 250 ml. of absolute ethanol are added dropwise. The resulting clear, light yellow solution is allowed to reflux for an additional 1 hour after complete addition of the methyl formyl benzoate/ethanol solution. The reaction solution is then stripped of excess hydrazine, ethanol, water and methanol on a rotary evaporator to yield a yellow solid. The solid is washed two times with 500 ml. portions of cold distilled water. The resultant white product is collected by filtration and dried at 100° C. and 3 mm. pressure for 12 hours. Analysis confirms the product is 4-(hydrazonomethyl)benzoic acid hydrazine.

The 4-(hydrazonomethyl)benzoic acid hydrazide can be prepared into a film-forming polymer which can be regarded as a poly(hydrazone-hydrazide) and is composed of recurring units of the structure

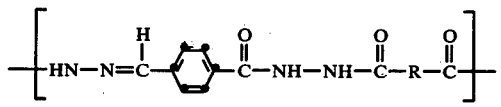

where R is a divalent alicyclic radical having 4 to 20 carbon atoms, a divalent aliphatic radical having 1 to 40 carbon atoms or a divalent aromatic radical having 6 to 16 carbon atoms.

Preferably R is the 1,4-phenylene or 1,3-phenylene radical.

This polymer can be prepared by condensation polymerization of equal moles of the 4-(hydrazonomethyl)-benzoic acid hydrazide of this invention having the structure

and a difunctional acid chloride having the structure

where R is the same as above.

Examples of difunctional acid chlorides that can be used to form the polymer of this invention include the diacid chloride derivatives of the following dicarboxylic acids: malonic, dimethylmalonic, succinic, glutaric, adipic, 2-methyladipic, trimethyladipic, pimelic, 2,2-dimethylglutaric, 3,3-diethylsuccinic, azelaic, sebacic, suberic, 1,3-cyclopentanedicarboxylic, 1,3-cyclohexanedicarboxylic, 1,4-cyclohexanedicarboxylic, terephthalic, isophthalic, 4-methylisophthalic, t-butylisophthalic, 2,5-norbornanedicarboxylic, 1,4-naphthalic, diphenic, 4,4'-oxydibenzoic, 4,4'-methylenedibenzoic, diglycolic, thiodipropionic, 4,4'-sulfonyldibenzoic; 2,5-naphthalenedicarboxylic; 2,6-naphthalenedicarboxylic, bibenzoic acid, bis(p-carboxyphenyl) methane; p-oxy(p- carboxyphenyl) benzoic acid, ethylene-bis(p-oxybenzoic acid), ethylene-bis-p-benzoic acid, tetramethylene-bis(p-oxybenzoic acid), and 1,5-naphthalene dicarboxylic acid. In a preferred embodiment the difunctional acid chloride is the dichloride derivative of terephthalic acid or isophthalic acid. Mixtures of these two materials can also be used. These compounds and their preparation are well known in the art.

The poly(hydrazone-hydrazide) of the invention can be prepared by the conventional condensation of 4-(hydrazonomethyl)benzoic acid hydrazide with difunctional acid chlorides by contacting the materials in a suitable inert reaction solvent at suitable thermodynamic conditions for a suitable time in accordance with the following reaction:

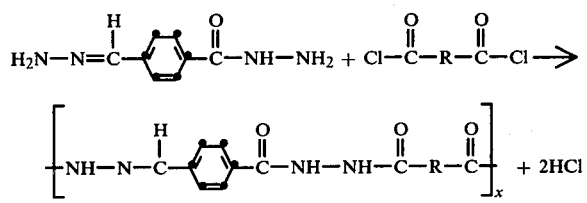

where R is as described above and x is an integer sufficient to achieve an inherent viscosity of at least 0.3.

The reaction solvent must be capable of dissolving but not destroying the 4-(hydrazonomethyl)benzoic acid hydrazide, the difunctional acid chloride and the resulting polymer of the invention. Examples of suitable reaction solvents include dimethylacetamide, N-methylpyrollidone and dimethylformamide. Dimethylacetamide is preferred.

The two materials can be contacted in the reaction solvent by techniques well known in the art, such as the slow addition of a solution of the difunctional acid chloride and a suitable solvent to a solution of the 4-hydrazonomethyl)benzoic acid hydrazide and a suitable solvent.

The temperature used for contacting the materials is not critical but should be high enough for the reaction to proceed at a reasonable speed. Since the reaction is exothermic, preferably the solution of the reaction solvent and the 4-(hydrazonomethyl)benzoic acid hydrazide is cooled prior to addition of the difunctional acid chloride.

Since HCl is produced in the reaction, an alkylene oxide, such as propylene oxide, can be added to the reaction mixture to neutralize the reaction mixture.

The resulting polymer can be recovered by conventional methods, such as pouring the reaction mixture into water.

An example of the preparation of poly(hydrazonehydrazide) is given below.

To a dry 500 ml. flask fitted with stirrer, nitrogen purge, and dropping funnel is charged 15 grams (0.084 mole) of 4-(hydrazonomethyl)benzoic acid hydrazide, and 200 ml. of dry dimethylacetamide which has been distilled and stored over molecular sieves. The solution is cooled to ~10° C. by use of an ice bath. Over a period of 30 minutes 17.1 grams (0.084 mole) of freshly distilled isophthaloyl chloride dissolved in 50 ml. of dimethylacetamide is slowly added. The solution becomes light yellow and highly viscous. The viscous material is stirred at room temperature for 1.5 hours after which 15 grams of propylene oxide are slowly added during very vigorous stirring. The clear viscous polymeric dope is coagulated by pouring into distilled water in a Waring blender operating at a high rate of speed. The white coagulated polymer is washed twice with water and once with acetone. The polymer is dried 6 hours at 120° C. and 1 mm pressure. Analysis shows the resulting polymer to be the poly(hydrazone-hydrazide) having an inherent viscosity of 0.83.

The polymers prepared from the 4-(hydrazonomethyl)benzoic acid hydrazide of this invention can be prepared into useful films by solvent casting techniques well known in the art wherein a solution of the polymer in a suitable solvent is poured onto a suitable surface, the solvent is allowed to evaporate and the film is removed from the surface. The same solvents useful as reaction solvents can be used as film casting solvents. The amount of polymer in the solution can vary widely but 10 weight percent, based on the weight of the solution, gives good results. The evaporation of the solvent is preferably accelerated by the use of heat, low pressure, or both.

A specific example of the preparation of film from the polymer described above is given below.

Films are cast from a solution of dimethylacetamide and 10 weight percent, based on the weight of the solution, of the above-described poly(hydrazone-hydrazide) by pouring the solution on a glass plate and drying the solution for 1 hour at 120° C. and 1 mm pressure followed by drying for 2 hours at 180°-200° C. and 1 mm pressure. The resultant flexible, clear, light yellow film has excellent tensile strength and tear strength as shown by the following properties:

| | |
|---|---|
| Tensile strength at break, ASTM D-882-73 | 19,600 psi |
| Initial tear strength, ASTM D-1004-66 | 1,100 g./mil. |
| Propagating tear strength, ASTM D-1938-67 | 24 g./mil. |

The film is tested further and confirmed to have a general overall balance of properties which are required for typical film applications as shown by the following properties:

| | |
|---|---|
| Tensile modulus, ASTM Standard D-882-73 | 620,000 psi |
| Elongation, ASTM Standard D-882-73 | 15% |
| Folding endurance, ASTM D-2176-69 | 960 double folds |

After 500 hours at 150° C. in a forced air oven the above film still retains a tensile strength at break of 17,200 psi and a flexural modulus of 576,000 psi.

Film samples are tested for solvent resistance by immersion in the following solvents at 23° C. and are shown to have excellent resistance to common solvents.

| | |
|---|---|
| Ethyl acetate | No effect after 100 days |
| Heptane | No effect after 100 days |
| Toluene | No effect after 100 days |
| Acetone | No effect after 100 days |
| Methyl ethyl ketone | No effect after 100 days |

The polymers which contain the 4-(hydrazonomethyl)benzoic acid hydrazide of this invention have an inherent viscosity of at least 0.3, preferably at least 0.5, measured at 25° C. using 0.50 grams of polymer per 100 ml. of dimethylacetamide.
I claim:
1. 4-(Hydrazonomethyl)benzoic acid hydrazide having the structure
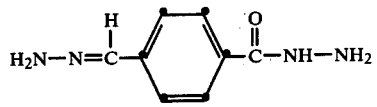
* * * * *